United States Patent
Nakamura et al.

(10) Patent No.: US 11,440,862 B2
(45) Date of Patent: *Sep. 13, 2022

(54) SOLVENT COMPOSITION, CLEANING METHOD, METHOD OF FORMING A COATING FILM, HEAT TRANSFER FLUID, AND HEAT CYCLE SYSTEM

(71) Applicant: AGC Inc., Chiyoda-ku (JP)

(72) Inventors: Masahiko Nakamura, Chiyoda-ku (JP); Hiroaki Mitsuoka, Chiyoda-ku (JP); Mari Ichinokawa, Chiyoda-ku (JP); Atsushi Fujimori, Chiyoda-ku (JP); Hidekazu Okamoto, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 94 days.

This patent is subject to a terminal disclaimer.

(21) Appl. No.: 17/020,652

(22) Filed: Sep. 14, 2020

(65) Prior Publication Data

US 2020/0407297 A1    Dec. 31, 2020

Related U.S. Application Data

(63) Continuation of application No. 16/515,770, filed on Jul. 18, 2019, now Pat. No. 10,807,926, which is a continuation of application No. 15/865,463, filed on Jan. 9, 2018, now Pat. No. 10,414,706, which is a continuation of application No. PCT/JP2016/062475, filed on Apr. 20, 2016.

(30) Foreign Application Priority Data

Jul. 27, 2015 (JP) ................................ 2015-148070
Jan. 15, 2016 (JP) .............................. JP2016-005952

(51) Int. Cl.

| | |
|---|---|
| *C07C 21/18* | (2006.01) |
| *C09D 201/00* | (2006.01) |
| *C09K 5/04* | (2006.01) |
| *C11D 7/50* | (2006.01) |
| *C11D 11/00* | (2006.01) |
| *C08B 3/08* | (2006.01) |
| *C09D 7/20* | (2018.01) |
| *C07C 21/22* | (2006.01) |
| *C09K 5/10* | (2006.01) |
| *C11D 3/43* | (2006.01) |
| *C07C 19/10* | (2006.01) |
| *C08K 5/02* | (2006.01) |

(52) U.S. Cl.
CPC ............ *C07C 21/18* (2013.01); *C07C 19/10* (2013.01); *C07C 21/22* (2013.01); *C08B 3/08* (2013.01); *C09D 7/20* (2018.01); *C09D 201/00* (2013.01); *C09K 5/044* (2013.01); *C09K 5/10* (2013.01); *C11D 3/43* (2013.01); *C11D 7/5018* (2013.01); *C11D 11/0017* (2013.01); *C08K 5/02* (2013.01); *C09K 2205/126* (2013.01)

(58) Field of Classification Search
CPC ......... C07C 21/18; C07C 19/10; C07C 21/22; C09D 7/20; C09D 201/00; C09K 5/044; C09K 5/10; C09K 2205/126; C11D 3/43; C11D 7/5018; C11D 11/0017; C11D 7/30; C08K 5/02; B08B 3/08; C08B 3/08
USPC ............................................ 252/67; 427/445
See application file for complete search history.

(56) References Cited

U.S. PATENT DOCUMENTS

| | | | |
|---|---|---|---|
| 5,316,690 A | * | 5/1994 | Li ............................. D06L 1/02 134/40 |
| 8,987,536 B2 | | 3/2015 | Sun et al. |
| 9,963,410 B2 | | 5/2018 | Karube et al. |
| 10,414,706 B2 | * | 9/2019 | Nakamura ........... C09D 201/00 |
| 10,472,307 B2 | * | 11/2019 | Nakamura .............. C07C 21/18 |
| 10,807,926 B2 | * | 10/2020 | Nakamura .............. C07C 21/18 |
| 10,975,008 B2 | * | 4/2021 | Nakamura .............. C07C 19/10 |

(Continued)

FOREIGN PATENT DOCUMENTS

| | | |
|---|---|---|
| CN | 102596869 A | 7/2012 |
| EP | 3 263 544 A1 | 1/2018 |

(Continued)

OTHER PUBLICATIONS

CAS reg. No. 212835-96-6, Oct. 18, 1998. (Year: 1998).*

(Continued)

*Primary Examiner* — Douglas J McGinty
(74) *Attorney, Agent, or Firm* — Oblon, McClelland, Maier & Neustadt, L.L.P.

(57) ABSTRACT

There are provided a solvent composition which is excellent in solubility of various organic substances and excellent in detergency and a drying property, and has no adverse effect on a global environment and is excellent in stability; a cleaning method using the solvent composition; a method of forming a coating film; a heat transfer fluid including the solvent composition; and a heat cycle system using the heat transfer fluid. A solvent composition including 1-chloro-2, 3,3-trifluoro-1-propene and 1-chloro-3,3-difluoro-1-propyne, a cleaning method of bringing the solvent composition and an article into contact with each other, a method of dissolving a nonvolatile organic compound in the solvent composition to produce a coating film-forming composition and evaporating the solvent composition after applying the coating film-forming composition on an article to be coated, to form a coating film, a heat transfer fluid including the solvent composition, and a heat cycle system using the heat transfer fluid.

6 Claims, 1 Drawing Sheet

(56) References Cited

U.S. PATENT DOCUMENTS

| | | | |
|---|---|---|---|
| 2007/0129579 A1 | 6/2007 | Wang et al. | |
| 2010/0145111 A1 | 6/2010 | Sharratt et al. | |
| 2011/0037016 A1 | 2/2011 | Singh et al. | |
| 2012/0161063 A1 | 6/2012 | Singh | |
| 2018/0044268 A1 | 2/2018 | Karube et al. | |
| 2018/0127341 A1 | 5/2018 | Nakamura et al. | |
| 2018/0162794 A1 | 6/2018 | Ichinokawa et al. | |
| 2018/0319726 A1 | 11/2018 | Mitsuoka et al. | |
| 2020/0407297 A1* | 12/2020 | Nakamura | C11D 11/0017 |

FOREIGN PATENT DOCUMENTS

| | | |
|---|---|---|
| JP | 2008-110980 | 5/2008 |
| JP | 2013-504658 | 2/2013 |
| JP | 2013-506731 | 2/2013 |
| JP | 2014-37425 | 2/2014 |
| JP | 2015-518898 | 7/2015 |
| WO | WO 2005/042451 A2 | 5/2005 |
| WO | WO 2008/075017 A2 | 6/2008 |
| WO | WO 2008/149907 A1 | 12/2008 |
| WO | WO 2011/031697 A2 | 3/2011 |
| WO | WO 2011/041286 A2 | 4/2011 |
| WO | WO 2013/184865 A1 | 12/2013 |
| WO | WO 2016/136744 A1 | 9/2016 |
| WO | WO 2017/018010 | 2/2017 |
| WO | WO 2017/018011 | 2/2017 |
| WO | WO 2017/122803 A1 | 7/2017 |
| WO | WO 2018/101323 A1 | 6/2018 |

OTHER PUBLICATIONS

CAS reg. No. 438547-44-5, Jul. 15, 2002. (Year: 2002).*

International Search Report dated Aug. 2, 2016 in PCT/JP2016/062475, filed on Apr. 20, 2016 (with English Translation).

Written Opinion dated Aug. 2, 2016 in PCT/JP2016/062475, filed on Apr. 20, 2016.

Anthony B. Bondi, et al. "Re-identification of $C_3HClF_2$ by analysis of its Diels-Alder products", Journal of Fluorine Chemistry 126, 2005, 4 pages.

* cited by examiner

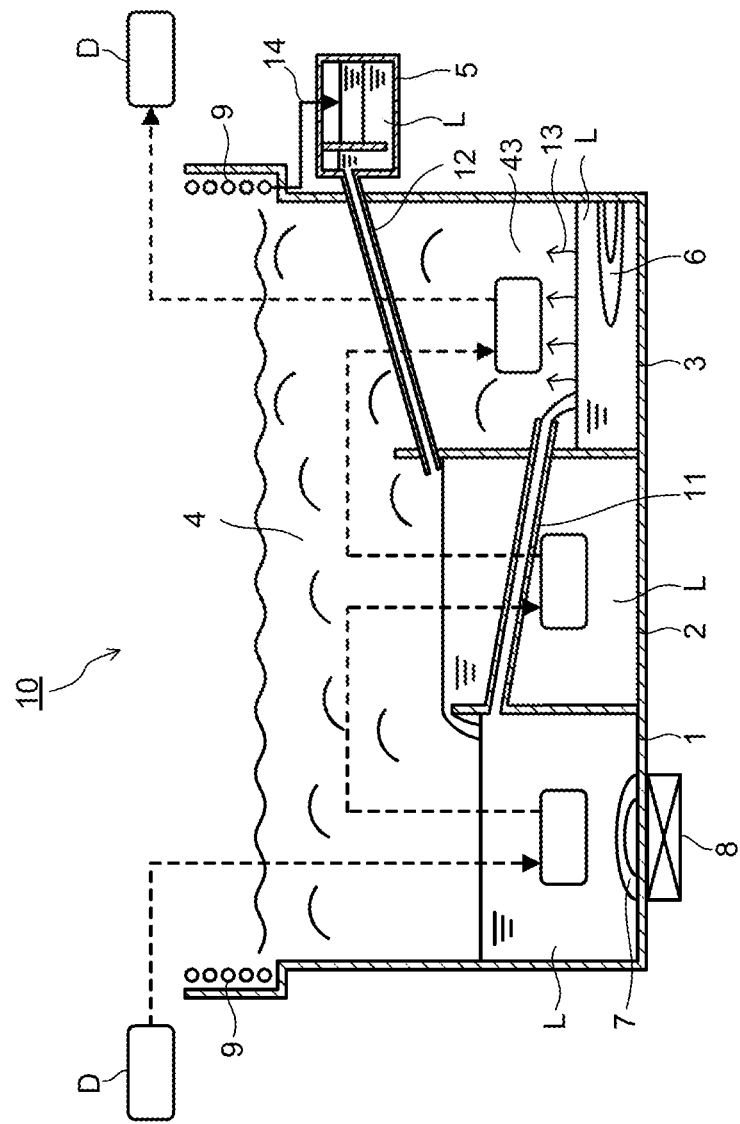

SOLVENT COMPOSITION, CLEANING METHOD, METHOD OF FORMING A COATING FILM, HEAT TRANSFER FLUID, AND HEAT CYCLE SYSTEM

CROSS-REFERENCE TO RELATED APPLICATIONS

This application is a continuation application of U.S. application Ser. No. 15/865,463, filed Jan. 9, 2018, which is in turn a continuation of prior International Application No. PCT/JP2016/062475, filed on Apr. 20, 2016 which is based upon and claims the benefit of priority from Japanese Patent Applications No. 2015-148070, filed on Jul. 27, 2015 and No. 2016-005952, filed on Jan. 15, 2016; the entire contents of all of which are incorporated herein by reference.

FIELD

The present invention relates to a solvent composition which is excellent in solubility of various organic substances and excellent in detergency and has a sufficient drying property, and has no adverse effect on a global environment and is excellent in stability. Specifically, the solvent composition of the present invention can be used in a wide range of uses, such as a cleaning solvent, a dilution coating solvent, and a heat transfer fluid.

BACKGROUND

In manufacture of IC, an electronic component, a precision machinery component, an optical component, and the like, in a manufacturing process, an assembly process, a final finishing process, and the like, components are cleaned by a cleaning solvent, thereby removing flux, a processing oil, wax, a release agent, dust, and the like adhering to the components. Further, as a method of manufacturing an article having a coating film containing various organic chemical substances such as a lubricant, for example, there is known a method in which a solution in which the organic chemical substances have been dissolved in a dilution coating solvent is prepared, the solution is applied on an article to be coated, and thereafter the dilution coating solvent is evaporated to form a coating film. The dilution coating solvent is required to allow the organic chemical substances to be dissolved sufficiently and to have a sufficient drying property as well.

As a solvent to be used in such uses, in that it has incombustibility and low toxicity, is excellent in stability, does not encroach on a base material of metal, plastic, elastomer, or the like, and is excellent in chemical and thermal stability, there has been used a fluorinated solvent or the like containing a chlorofluorocarbon (hereinafter, mentioned as "CFC") such as 1,1,2-trichloro-1,2,2-trifluoroethane, a hydrochlorofluorocarbon (hereinafter, mentioned as "HCFC") such as 2,2-dichloro-1,1,1-trifluoroethane, 1,1-dichloro-1-fluoroethane, 3,3-dichloro-1,1,1,2,2-pentafluoropropane, and 1,3-dichloro-1,1,2,2,3-pentafluoropropane, or the like.

However, because the CFCs and the HCFCs are chemically very stable, they each have a long lifetime in the troposphere after vaporization, and diffuse and reach the stratosphere. Therefore, there is a problem that the CFCs and the HCFCs which have reached the stratosphere are decomposed by ultraviolet rays and generate chlorine radicals to deplete an ozone layer.

On the other hand, as a solvent having no chlorine atom and having no adverse effect on the ozone layer, a perfluorocarbon (hereinafter, mentioned as "PFC") is known. In addition, as an alternative solvent to the CFCs and the HCFCs, a hydrofluorocarbon (hereinafter, mentioned as "HFC"), a hydrofluoroether (hereinafter, mentioned as "HFE"), and the like are also under development. However, because the HFCs and the PFCs have a high global warming potential, they are substances subject to regulation by the Kyoto Protocol.

As a new solvent substituted for the solvents of the HFCs, the HFEs, and the PFCs, a fluoroolefin having a double bond between carbon atoms is proposed. Because the fluoroolefin has a short lifetime in the atmosphere due to easy decomposition and its ozone depletion potential and global warming potential are low, it has an excellent property in which an effect on a global environment is small, but on the other hand, it is poor in stability due to the easy decomposition, and there has been a problem that in a case of use as the cleaning solvent or the dilution coating solvent, it decomposes and acidifies in use.

Therefore, in Patent References 1 (JP-A No. 2013-504658) and 2 (JP-A No. 2013-506731), there is disclosed a technology of adding additional components as a lubricant, a stabilizer, a metal passivator, a corrosion inhibitor, a flame inhibitor, and other compound and/or component for regulating a specific property of a composition to a wide variety of fluoroolefins which each include 1-chloro-2,3,3-trifluoro-1-propene and each have a double bond between carbon atoms. However, Patent References 1 and 2 do not mention a technology of stabilizing 1-chloro-2,3,3-trifluoro-1-propene by adding 1-chloro-3,3-difluoro-1-propyne to 1-chloro-2,3,3-trifluoro-1-propene.

SUMMARY

In the present invention, it is an article thereof to provide: a solvent composition which is excellent in solubility of various organic substances and excellent in detergency and has a sufficient drying property, and has no adverse effect on a global environment and is excellent in stability; a cleaning method using the solvent composition; a method of forming a coating film using the solvent composition; a heat transfer fluid including the solvent composition; and a heat cycle system using the heat transfer fluid.

The present inventors have performed studies in consideration of the above-described points, resulting in completing the present invention. That is, the present invention consists of the following.

[1] A solvent composition including 1-chloro-2,3,3-trifluoro-1-propene and 1-chloro-3,3-difluoro-1-propyne.

[2] The solvent composition according to [1], wherein a proportion of a content of 1-chloro-3,3-difluoro-1-propyne to a total of a content of the 1-chloro-2,3,3-trifluoro-1-propene and a content of the 1-chloro-3,3-difluoro-1-propyne is 0.0001 to 0.1 mass %.

[3] The solvent composition according to [1], wherein a proportion of a content of 1-chloro-2,3,3-trifluoro-1-propene to a total amount of the solvent composition is 80 mass % or more.

[4] The solvent composition according to [1], wherein the 1-chloro-2,3,3-trifluoro-1-propene consists of (Z)-1-chloro-2,3,3-trifluoro-1-propene and (E)-1-chloro-2,3,3-trifluoro-1-propene, and a proportion of a content of (Z)-1-chloro-2,3,3-trifluoro-1-propene to a total amount of 1-chloro-2,3,3-trifluoro-1-propene is 80 to 100 mass %.

[5] A cleaning method including bringing the solvent composition according to [1] and an article to be cleaned into contact with each other.

[6] The cleaning method according to [5], wherein a processing oil adhering to the article to be cleaned is cleaned.

[7] The cleaning method according to [6], wherein the processing oil is at least one selected from a group consisting of a cutting oil, a quenching oil, a rolling oil, a lubricating oil, a machine oil, a presswork oil, a stamping oil, a drawing oil, an assembly oil, and a wire drawing oil.

[8] The cleaning method according to [5], wherein the article to be cleaned is clothing.

[9] A method of forming a coating film including dissolving a nonvolatile organic compound in the solvent composition according to [1] to prepare a coating film-forming composition and evaporating the solvent composition after applying the coating film-forming composition on an article to be coated, to form a coating film consisting of the nonvolatile organic compound.

[10] A heat transfer fluid including the solvent composition according to [1].

[11] A heat cycle system using the heat transfer fluid according to [10].

A solvent composition of the present invention is excellent in solubility of various organic substances and excellent in detergency and has a sufficient drying property, and has no adverse effect on a global environment and is excellent in stability. A cleaning method of the present invention has no adverse effect on a global environment and is excellent in detergency. A method of forming a coating film of the present invention has no adverse effect on a global environment and allows a uniform coating film to be formed. A heat transfer fluid including the solvent composition of the present invention has no adverse effect on a global environment and is excellent in stability. A heat cycle system using the heat transfer fluid of the present invention has no adverse effect on a global environment.

BRIEF DESCRIPTION OF THE DRAWINGS

The FIGURE is a view schematically illustrating one example of a cleaning apparatus carrying out a cleaning method of the present invention.

MODE FOR CARRYING OUT THE INVENTION

<Solvent Composition>
A solvent composition of the present invention includes 1-chloro-2,3,3-trifluoro-1-propene (CHCl=CF—CHF$_2$, hereinafter mentioned as "HCFO-1233yd") and 1-chloro-3,3-difluoro-1-propyne (CCl≡C—CHF$_2$).

In the solvent composition of the present invention, HCFO-1233yd is a component having an excellent property described below as a solvent, and 1-chloro-3,3-difluoro-1-propyne is a component included in the solvent composition as a stabilizer stabilizing HCFO-1233yd.

(HCFO-1233yd)
Because HCFO-1233yd is fluoroolefin having a double bond between carbon atoms, its lifetime in the atmosphere is short and its ozone depletion potential and global warming potential are low.

In HCFC-1233yd, a Z-isomer and an E-isomer which are a geometric isomer exist according to positions of substituents on the double bond. When the compound name or an abbreviated name of the compound is used unless otherwise stated in this description, at least one selected from the Z-isomer and the E-isomer is indicated, and when (E) or (Z) is denoted behind the compound name or the abbreviated name of the compound, an (E)-isomer or a (Z)-isomer of each compound is indicated. For example, HCFO-1223yd (Z) indicates the Z-isomer, and HCFO-1233yd(E) indicates the E-isomer.

A boiling point of HCFO-1233yd(Z) is about 54° C., a boiling point of HCFO-1233yd(E) is about 48° C., and both are substances excellent in a drying property. Further, even though they are boiled to turn into vapor, even parts susceptible to heat, such as resin parts, are not easily adversely affected since the boiling point of HCFO-1233yd(Z) is about 54° C. and the boiling point of HCFO-1233yd(E) is about 48° C. In addition, HCFO-1233yd has excellent ability as a cleaning solvent or a coating solvent, such as no flash point, low surface tension and viscosity, and easy evaporation even at a normal temperature.

Note that in this description, the boiling points of the compounds are boiling points at a normal pressure unless otherwise stated. In this description, the normal pressure means 760 mmHg and the normal temperature means 25° C., respectively.

On the other hand, HCFO-1233yd does not have sufficient stability and when HCFO-1233yd is retained at the normal temperature and the normal pressure, it decomposes in several days to generate chlorine ions. Therefore, in the solvent composition of the present invention, stabilization of HCFO-1233yd is achieved by containing the later-described 1-chloro-3,3-difluoro-1-propyne with HCFO-1233yd.

In the solvent composition of the present invention, a proportion of a content of HCFO-1233yd is preferably 50 mass % or more, more preferably 80 mass % or more and further preferably 90 mass % or more to a total amount of the solvent composition. As long as the proportion is equal to or more than the above lower limit value, the solvent composition is excellent in solubility of various organic substances and detergency. The content of HCFO-1233yd is particularly preferably an amount in which a content of 1-chloro-3,3-difluoro-1-propyne has been removed from the total amount of the solvent composition. That is, the solvent composition particularly preferably consists of only HCFO-1233yd and 1-chloro-3,3-difluoro-1-propyne. However, the solvent composition may contain a component which is produced in a manufacturing process of HCFO-1233yd and is difficult to separate from HCFO-1233yd and/or a component which is produced in a manufacturing process of 1-chloro-3,3-difluoro-1-propyne and is difficult to separate from 1-chloro-3,3-difluoro-1-propyne in a range in which an effect of the present invention is not impaired, for example, by an amount which is 10 mass % or less with respect to the total amount of the solvent composition.

In the solvent composition of the present invention, in the Z-isomer and the E-isomer of HCFO-1233yd, HCFO-1233yd(Z) is preferable in that it has the boiling point higher than that of HCFO-1233yd(E) and does not easily volatilize at the normal temperature. Therefore, a proportion of a content of HCFO-1233yd(Z) to a total amount of HCFO-1233yd is preferably 80 to 100 mass %, and more preferably 90 to 100 mass %. As long as the proportion is in the above range, a loss due to volatilization of the solvent composition is suppressed, which leads to a reduction in usage, thereby being excellent in economic efficiency. However, an upper limit value of the proportion of the content of HCFO-1233yd (Z) is particularly preferably about 99.9 mass % to the total amount of HCFO-1233yd from the viewpoint of suppressing an increase in a manufacturing cost due to a distillation separation of the Z-isomer and the E-isomer of HCFO-1233yd, or the like.

HCFO-1233yd can be manufactured by subjecting, for example, industrially stably obtainable 1-chloro-2,2,3,3-tetrafluoropropane ($CHF_2$—$CF_2$—CHFCl, hereinafter, mentioned as "HCFC-244ca") to a dehydrofluorination reaction. According to this method, HCFO-1233yd is produced by the dehydrofluorination reaction at temperatures of 50 to 80° C., using HCFC-244ca as a raw material and using potassium hydroxide or sodium hydroxide as a reactant.

In the produced HCFO-1233yd, HCFO-1233yd(Z) and HCFO-1233yd(E) which are a structural isomer exist, and in this manufacturing method, HCFO-1233yd(Z) is produced more than HCFO-1233yd(E). These isomers can be separated into HCFO-1233yd(Z) and HCFO-1233yd(E) in a purification process thereafter.

Note that in the solvent composition of the present invention, a roughly purified product of HCFO-1233yd which is obtained by appropriately purifying the reaction solution including HCFO-1233yd produced in the above and includes the component difficult to separate from HCFO-1233yd other than HCFO-1233yd to such an extent that the effect of the present invention is not impaired may be used. If the roughly purified product of HCFO-1233yd is used, a cost of the distillation separation or the like is reduced, which is preferable.

As the component difficult to separate from HCFO-1233yd which is included in the reaction solution which is obtained by the above-described manufacturing method and includes HCFO-1233yd, HCFC-244ca which is the raw material, or the like can be cited. A boiling point of HCFC-244ca is about 53° C. and close to the boiling point of HCFO-1233yd(Z), and therefore when HCFO-1233yd is used as HCFO-1233yd(Z) or as an isomer mixture of HCFO-1233yd, in particular, HCFC-244ca can be included in the roughly purified product.

When the above-described roughly purified product of HCFO-1233yd is used, a proportion of a content of HCFC-244ca in the solvent composition is preferably 1 mass % or less to the total amount of the solvent composition from the viewpoint of an environmental load. Further, if HCFC-244ca is included in the solvent composition, the proportion of the content of HCFC-244ca is preferably 0.0001 to 1 mass %, more preferably 0.005 to 1 mass %, and further preferably 0.01 to 0.05 mass % to a total of the content of HCFO-1233yd and the content of HCFC-244ca from the viewpoint of the environmental load and a separation cost.

(1-chloro-3,3-difluoro-1-propyne)

1-chloro-3,3-difluoro-1-propyne is fluorocarbon having a triple bond between carbon atoms, and its ozone depletion potential and global warming potential are low. 1-chloro-3,3-difluoro-1-propyne is soluble in HCFO-1233yd. 1-chloro-3,3-difluoro-1-propyne is considered to have a function as a stabilizer suppressing decomposition of HCFO-1233yd(Z) and HCFO-1233yd(E) and stabilizing them by an effect which is not necessarily clear but is presumed to be capture of radicals.

Note that in this description, solubility of a certain substance in HCFO-1233yd means a property capable of dissolving the substance uniformly without causing a two-layer separation and turbidity by mixing it with HCFO-1233yd and stirring it at the normal temperature (25° C.) so as to become a desired concentration.

Further, the stability in the solvent composition of the present invention can be evaluated by, for example, providing a chlorine ion concentration after retaining the solvent composition for a certain period as an index. The solvent composition of the present invention containing 1-chloro-3,3-difluoro-1-propyne with HCFO-1233yd allows the chlorine ion concentration in the solvent composition which is measured after retaining the solvent composition at 50° C. for three days to be suppressed to less than 100 ppm, for example. Note that regulating an amount of 1-chloro-3,3-difluoro-1-propyne with respect to HCFO-1233yd in the solvent composition also makes it possible to set a chlorine ion generation amount in a case of evaluation similar to that in the above to less than 50 ppm or less than 10 ppm.

A content of 1-chloro-3,3-difluoro-1-propyne in the solvent composition of the present invention is not limited as long as it is an amount in which HCFO-1233yd is capable of exhibiting the above-described ability as a solvent and the stabilization of HCFO-1233yd is kept. A proportion of the content of 1-chloro-3,3-difluoro-1-propyne in the solvent composition is preferably 0.0001 to 0.1 mass % and more preferably 0.0001 to 0.001 mass % to a total of the content of HCFO-1233yd and the content of 1-chloro-3,3-difluoro-1-propyne. As long as the proportion is in the above-described range, the stability of the solvent composition is further excellent.

1-chloro-3,3-difluoro-1-propyne can be manufactured by, for example, the following method (A) or method (B).

The method (A) is a method mentioned in a non-patent document Journal of Fluoro Chem 126 (2005), pages 1549 to 1552. Specifically, it is the method of manufacturing 1-chloro-3,3-difluoro-1-propyne by subjecting 1,2-dichloro-3,3-difluoro-1-propene (CHCl═CCl—$CHF_2$) to a dehydrochlorination reaction using a base as a catalyst.

The method (B) is a method of manufacturing 1-chloro-3,3-difluoro-1-propyne by using HCFO-1233yd as a raw material instead of 1,2-dichloro-3,3-difluoro-1-propene in the method (A) and subjecting it to a dehydrofluorination reaction (hereinafter, "dehydrofluorination reaction (2)"). Note that regulating a condition when HCFO-1233yd is manufactured by using HCFC-244ca as the raw material and subjecting it to the dehydrofluorination reaction (hereinafter, "dehydrofluorination reaction (1)") allows the dehydrofluorination reaction (2) to be promoted simultaneously with the dehydrofluorination reaction (1).

Thus, according to the method (hereinafter, referred to as a method (B')) in which the dehydrofluorination reaction (1) and the dehydrofluorination reaction (2) are simultaneously promoted using HCFC-244ca as the raw material, a reaction solution containing HCFO-1233yd and 1-chloro-3,3-difluoro-1-propyne together can be obtained. Regulating a reaction condition in the method (B') also makes it possible to make a relationship of the content between HCFO-1233yd and 1-chloro-3,3-difluoro-1-propyne in the reaction solution to be produced similar to a desirable relationship of the content between both in the solvent composition of the present invention.

Note that 1-chloro-3,3-difluoro-1-propyne is close to HCFO-1233yd, particularly HCFO-1233yd(E) in the boiling point. Accordingly, it is also possible to separate a mixture which includes HCFO-1233yd and 1-chloro-3,3-difluoro-1-propyne together and in which a content of a component other than these is reduced to an amount in which the effect of the present invention is not impaired from the reaction solution to be produced by the method (B'), and it is also possible to use the mixture as it is as the solvent composition of the present invention.

In the present invention, in terms of production efficiency, 1-chloro-3,3-difluoro-1-propyne is preferably the one to be obtained by the method (B), and more preferably the one to be obtained by the method (B').

By the method (B'), HCFO-1233yd and 1-chloro-3,3-difluoro-1-propyne are produced. From the reaction solution to be obtained by the method (B'), HCFO-1233yd(Z), HCFO-1233yd(E), and 1-chloro-3,3-difluoro-1-propyne may be each isolated and used for the solvent composition of the present invention, or may be used as a mixture including two or more of these for the solvent composition.

Here, as described above, HCFO-1233yd(E) and 1-chloro-3,3-difluoro-1-propyne are close to each other in the boiling point, and purification equipment and purification techniques having high accuracy are required for a separation of both, in particular, isolation of 1-chloro-3,3-difluoro-1-propyne. Accordingly, it is preferable from the viewpoint of manufacturing cost reduction and production efficiency improvement to separate each of a mixture of HCFO-1233yd(E) and 1-chloro-3,3-difluoro-1-propyne, and HCFO-1233yd(Z) from the reaction solution to be obtained by the method (B'), use these, and regulate the content of each of the components in the solvent composition of the present invention. Note that since isolation of HCFO-1233yd(E) is easier compared with the isolation of 1-chloro-3,3-difluoro-1-propyne from the reaction solution to be obtained by the method (B'), HCFO-1233yd(E) may be isolated from the reaction solution to be obtained by the method (B') and used for the solvent composition of the present invention as necessary.

As the above-described mixture of HCFO-1233yd(E) and 1-chloro-3,3-difluoro-1-propyne, for example, the mixture including an amount in which 1-chloro-3,3-difluoro-1-propyne is set to 0.1 to 10 mass % with respect to a total of the content of HCFO-1233yd(E) and the content of 1-chloro-3,3-difluoro-1-propyne is preferable in terms of the production efficiency improvement.

(Optional Component)

The solvent composition of the present invention may contain components (hereinafter, simply referred to as "other component") other than HCFO-1233yd, 1-chloro-3,3-difluoro-1-propyne, and the above-described component which is produced in the manufacturing process of HCFO-1233yd or 1-chloro-3,3-difluoro-1-propyne and is difficult to separate from HCFO-1233yd or 1-chloro-3,3-difluoro-1-propyne in the range in which the effect of the present invention is not impaired. The other components may be components (however, 1-chloro-3,3-difluoro-1-propyne is excluded, and hereinafter, referred to as "other solvent") which are used depending on various purposes such as enhancing of the solubility and regulating of an evaporation rate, are soluble in HCFO-1233yd, and function as a solvent other than HCFO-1233yd, for example.

The other components may be stabilizers (hereinafter, referred to as "other stabilizer") other than 1-chloro-3,3-difluoro-1-propyne stabilizing HCFO-1233yd, for example.

As the other stabilizers, there can be cited at least one selected from a group consisting of phenols, ethers, epoxides, amines, alcohols, and hydrocarbons. The stabilizer may be one or a combination of two or more.

As the phenols, phenol, 1,2-benzendiol, 2,6-di-tert-butyl-4-methylphenol, m-cresol, 2-isopropyl-5-methylphenol, α-tocopherol, and 2-methoxyphenol are preferable.

As the ethers, cyclic ethers having 4 to 6 members are preferable, and among them, 1,4-dioxane, 1,3-dioxane, 1,3,5-trioxane, 2-methylfuran, and tetrahydrofuran are preferable.

As the epoxides, 1,2-propylene oxide, 1,2-butylene oxide, and butyl glycidyl ether are preferable.

As the amines, alkylamine and cyclic amines are preferable, and among them, pyrrole, N-methylpyrrole, 2-methylpyridine, n-propylamine, diisopropylamine, N-methylmorpholine, and N-ethylmorpholine are preferable.

As the alcohols, methanol, ethanol, isopropyl alcohol, and 2-propyne-1-ol which are linear or branched-chained alcohols having 1 to 3 carbon atoms are preferable.

As the hydrocarbons, regarding saturated hydrocarbons, n-pentane, cyclopentane, n-hexane, cyclohexane, and n-heptane are preferable. Regarding unsaturated hydrocarbon, 2-methyl-2-butene, 2-methyl-1-pentene, 2-methyl-2-pentene, 3-ethyl-2-butene, 2,3-dimethyl-2-butene, 2,4,4-trimethyl-1-pentene, and 2,4,4-trimethyl-2-pentene are preferable.

Among these, in terms of stability, 2-methyl-1-pentene, 2-methyl-2-pentene, 3-ethyl-2-butene, 2,3-dimethyl-2-butene, 2,4,4-trimethyl-1-pentene, 2,4,4-trimethyl-2-pentene, N-methylpyrrole, and 2-propyne-1-ol are further preferable.

When the solvent composition of the present invention is in contact with copper or a copper alloy, it may contain nitro compounds and triazoles in order to avoid corrosion of the above metals.

A content of the other components in the solvent composition of the present invention is appropriately regulated depending on types of the other components in the range in which the effect of the present invention is not impaired. A proportion of the content in a case of containing the other components is preferably about 1 mass % or less and more preferably 0.1 mass % or less for each of the components to the total amount of the solvent composition. Further, a total of the content of the other components is preferably 10 mass % or less, and more preferably 1 mass % or less.

The solvent composition of the present invention is a stable solvent composition which is excellent in solubility of various organic substances and excellent in detergency and has a sufficient drying property, and has no adverse effect on a global environment and is stabilized to suppress decomposition, and the solvent composition is preferably used for cleaning uses such as degreasing cleaning, flux cleaning, precision cleaning, and dry cleaning. In addition, the solvent composition of the present invention can be used in uses for which a coating film-forming composition is produced by dissolving a lubricant such as a silicone-based lubricant or a fluorine-based lubricant, an antirust made from a mineral oil or a synthetic oil, a moisture-proof coating agent for conducting water repellent treatment, or an antifouling coating agent such as a fingerprint removing/preventing agent for conducting antifouling treatment and a coating film is formed by applying the coating film-forming composition on an article surface. Moreover, the solvent composition of the present invention is suitable also as a heat transfer fluid for heating or cooling an article.

The articles to which the solvent composition of the present invention is applicable can be widely used for electronic components such as a capacitor, a diode, and a substrate on which these have been mounted, optical components such as a lens and a polarizing plate, automotive parts such as a fuel injection needle to be used for an engine unit and a gear of a drive unit in an automobile, parts of a drive unit to be used for an industrial robot, machine parts such as exterior parts, a carbide tool to be used for a machine tool such as a cutting tool, and the like. Moreover, as materials to which the solvent composition of the present invention is applicable, a wide range of materials such as metal, plastic, elastomer, glass, ceramics, and fabric can be cited, and among them, the solvent composition is suitable for metals such as iron, copper, nickel, gold, silver, and platinum, a sintered metal, glass, a fluorocarbon resin, and engineering plastic such as PEEK.

<Cleaning Method>

A cleaning method of the present invention is a method of cleaning extraneous matter adhering to an article to be cleaned by using the above-described solvent composition of the present invention, and is characterized by bringing the solvent composition of the present invention and the article to be cleaned into contact with each other.

In the cleaning method of the present invention, as the extraneous matter to be removed by cleaning, there can be cited flux; processing oils such as a cutting oil, a quenching oil, a rolling oil, a lubricating oil, a machine oil, a presswork oil, a stamping oil, a drawing oil, an assembly oil, and a wire drawing oil; a release agent; dust, and the like adhering to various articles to be cleaned. Because the present solvent composition is more excellent in solubility of the processing oil compared with HFC and HFE which are conventional solvent compositions, and the like, it is preferably used for cleaning of the processing oil.

Further, the solvent composition of the present invention is applicable to cleaning of the articles to be cleaned made of various materials such as metal, plastic, elastomer, glass, ceramics, and composite materials of these, and a fabric made of natural fiber or synthetic fiber. Here, as a more specific example of the articles to be cleaned, there can be cited fiber products, medical appliances, electric equipment, precision instruments, optical articles, their parts, and the like. As a specific example of the electric equipment, the precision instruments, the optical articles, and their parts, there can be cited an IC, a capacitor, a printed-circuit board, a micromotor, a relay, a bearing, an optical lens, a glass substrate, and the like.

The cleaning method of the article to be cleaned using the solvent composition of the present invention is not particularly limited except to bring the solvent composition of the present invention and the article to be cleaned into contact with each other. The contact makes it possible to remove dirt adhering to a surface of the article to be cleaned. As a specific cleaning method, for example, it is sufficient to employ manual cleaning, immersion cleaning, spray cleaning, immersion-oscillation cleaning, immersion ultrasonic cleaning, steam cleaning, methods by combining these, and the like. Cleaning conditions such as contact time, the number of times, and a temperature of the solvent composition of the present invention at a time of cleaning in these cleaning methods may be appropriately selected depending on the cleaning methods. Further, also regarding a cleaning apparatus, the publicly known one can be appropriately selected depending on each of the cleaning methods. As long as the solvent composition of the present invention is used for these cleaning methods, it is possible to repeatedly use it for a long period while maintaining detergency with almost no decomposition of the components.

The cleaning method of the present invention is applicable to, for example, a cleaning method having a solvent contact step in which the article to be cleaned is brought into contact with a liquid-phase solvent composition and a steam contact step in which after the solvent contact step, the article to be cleaned is exposed to steam generated by evaporating the solvent composition. As the cleaning apparatus applicable to such a cleaning method and the cleaning methods, for example, a cleaning method and a cleaning apparatus indicated in International Publication WO 2008/149907 can be cited.

The FIGURE is a view schematically illustrating one example of a cleaning apparatus similar to the cleaning apparatus which carries out the cleaning method having the above-described solvent contact step and steam contact step and is indicated in International Publication WO 2008/149907. A cleaning apparatus 10 includes a cleaning tank 1, a rinse tank 2, and a steam generation tank 3 in each of which a solvent composition L is housed. Moreover, the cleaning apparatus 10 includes, above these tanks, a steam zone 4 which is filled with steam generated from the solvent composition L, cooling tubes 9 which cool the steam, and a water separation tank 5 for subjecting the solvent composition L obtained by being condensed by the cooling tubes 9 and water adhering to the cooling tubes to a stationary separation. In actual cleaning, an article to be cleaned D is put in a dedicated jig or basket, or the like, and the cleaning is completed while moving the article to be cleaned D in order of the cleaning tank 1, the rinse tank 2, and a steam zone 43 immediately above the steam generation tank 3 in the cleaning apparatus 10.

A heater 7 and an ultrasonic vibrator 8 are included in a lower portion of the cleaning tank 1. In the cleaning tank 1, a temperature of the solvent composition L is raised by heating with the heater 7, physical force is imparted to the article to be cleaned D by cavitation generated by the ultrasonic vibrator 8 while controlling a constant temperature, and dirt adhering to the article to be cleaned D is removed by cleaning. At this time, as the physical force, other than an ultrasonic wave, any method which has been employed for previous cleaning machines, such as oscillation or a submerged jet of the solvent composition L, may be used. Note that in the cleaning of the article to be cleaned D in the cleaning tank 1, the ultrasonic vibration is not essential, and the cleaning may be performed without the ultrasonic vibration as necessary.

In the rinse tank 2, by immersing the article to be cleaned D in the solvent composition L, dirt components adhering to the article to be cleaned D in a state of dissolving in the solvent composition L are removed. The cleaning apparatus 10 has a design in which an overflow of the solvent composition L housed in the rinse tank 2 flows into the cleaning tank 1. Further, the cleaning tank 1 includes a pipe 11 which feeds the solvent composition L to the steam generation tank 3 in order to prevent a solution level from becoming equal to or more than a predetermined height.

In a lower portion of the steam generation tank 3, a heater 6 which heats the solvent composition L in the steam generation tank 3 is included. The solvent composition L housed in the steam generation tank 3 is boiled by heating with the heater 6, part or the whole of its composition becomes steam to rise upward as illustrated by arrows 13, and the steam zone 43 filled with the steam is formed immediately above the steam generation tank 3. The article to be cleaned D for which the cleaning in the rinse tank 2 has been completed is transported to the steam zone 43 and cleaned by the steam through an exposure to the steam (steam contact step).

Further, in the cleaning apparatus 10, an upper space of the tanks is used in common as the steam zone 4. The steam generated from the cleaning tank 1, the rinse tank 2, and the steam generation tank 3 is collected from the steam zone 4 as the solvent composition L by being cooled and condensed by the cooling tubes 9 provided in an upper portion of a wall surface of the cleaning apparatus 10. Thereafter, the aggregated solvent composition L is housed in the water separation tank 5 via a pipe 14 connecting the cooling tubes 9 and the water separation tank 5. In the water separation tank 5, water mixing in the solvent composition L is separated. The solvent composition L from which the water has been separated is returned to the rinse tank 2 through a pipe 12 connecting the water separation tank 5 and the rinse tank 2. In the cleaning apparatus 10, such a mechanism allows a reduction in an evaporation loss of the solvent composition.

When cleaning is performed in the cleaning apparatus 10 by using the solvent composition of the present invention, a temperature of the solvent composition of the present invention in the cleaning tank 1 is preferably set to 25° C. or more and less than the boiling point of the solvent composition. As long as the temperature is in the above-described range, it is possible to easily perform the degreasing cleaning of a processing oil or the like, and a cleaning effect by the ultrasonic wave is high. Further, a temperature of the solvent composition of the present invention in the rinse tank 2 is preferably 10 to 45° C. As long as the temperature is in the above-described range, a difference between a temperature of the article and a temperature of the steam of the solvent composition can be obtained sufficiently in a steam cleaning step, and therefore a sufficient amount of the solvent composition can be condensed on an article surface for steam cleaning, thereby resulting in a high rinsing effect. In addition, the temperature of the solvent composition of the present invention in the cleaning tank 1 is preferably higher than the temperature of the solvent composition in the rinse tank 2 in terms of detergency.

<Dry Cleaning Method>

Next, a case of using the solvent composition of the present invention for removal cleaning of dirt of various clothing will be described. The solvent composition of the present invention is suitable as a cleaning solvent for the clothing, namely, a dry cleaning solvent.

There can be cited cleaning and removing of dirt adhering to clothing such as a shirt, a sweater, a jacket, a skirt, trousers, a windbreaker, gloves, a muffler, and a stole, as a dry cleaning application using the solvent composition of the present invention.

Moreover, the solvent composition of the present invention is applicable to dry cleaning of the clothing made of fibers such as cotton, hemp, wool, rayon, polyester, acryl, and nylon.

Further, it is found that since HCFO-1233yd included in the solvent composition of the present invention includes a chlorine atom in its molecule, it has high solubility of the dirt and has cleaning power nearly equal to that of HCFCs such as HCFC-225 (dichloropentafluoropropane) having a wide range of solvency, with respect to oil and fat dirt.

Moreover, when the solvent composition of the present invention is used as the dry cleaning solvent, it is possible to compound soap in order to enhance the ability to remove water-soluble dirt such as sweat or mud, and to use the resultant product as a dry cleaning solvent composition. The soap indicates a surfactant to be used for the dry cleaning, and a cationic, nonionic, anionic, or ampholytic surfactant or the like is preferably used. It is found that since HCFO-1233yd has a chlorine atom in its molecule, it has a wide range of solubility to various organic compounds, and it is not required to optimize the soap depending on the solvent as HFEs and HFCs are required, which allows use of various soaps. Hence, the dry cleaning solvent composition using the solvent composition of the present invention can include at least one type of the surfactant selected from a group consisting of the cationic surfactant, the nonionic surfactant, the anionic surfactant, and the ampholytic surfactant.

As a specific example of the soaps, there can be cited a quaternary ammonium salt such as dodecyldimethylammonium chloride or trimethylammonium chloride as the cationic surfactant. There can be cited a surfactant such as polyoxyalkylene nonylphenyl ether, polyoxyalkylene alkyl ether, fatty acid alkanolamide, glycerin fatty acid ester, sorbitan fatty acid ester, sucrose fatty acid ester, propylene glycol fatty acid ester, or ester of phosphoric acid and fatty acid as the nonionic surfactant. There can be cited an alkyl sulfate such as a polyoxyethylene alkyl sulfate, a carboxylate such as a fatty acid salt (so-called soap), or a sulfonate such as an α-olefin sulfonate or a lauryl sulfate as the anionic surfactant. There can be cited a betaine compound such as alkylbetaine as the ampholytic surfactant.

A proportion of the content of the soap in the dry cleaning solvent composition is 0.01 to 10 mass %, preferably 0.1 to 5 mass %, and further preferably 0.2 to 2 mass % to a total amount of the solvent composition included in the dry cleaning solvent composition.

According to the above-explained cleaning method of the present invention, using the above-described solvent composition of the present invention suppresses decomposition of the solvent composition and allows repeated cleaning for a long period. In addition, as long as the solvent composition of the present invention is used, it is also possible to appropriately combine regeneration operations such as distillation regeneration and filtration regeneration, gas recovery in which scattered steam of the solvent composition is recovered, and the like without problems.

<Forming Method of Coating Film>

The solvent composition of the present invention can be used for a solvent (dilution coating solvent) for dilution coating of a nonvolatile organic compound. That is, a method of forming a coating film of the present invention is characterized by dissolving a nonvolatile organic compound in the above-described solvent composition of the present invention to prepare a coating film-forming composition and evaporating the solvent composition after applying the coating film-forming composition on an article to be coated, to form a coating film consisting of the nonvolatile organic compound.

Here, the nonvolatile organic compound in the present invention means the one which has a boiling point higher than that of the solvent composition of the present invention and in which the organic compound still remains on a surface even after evaporation of the solvent composition. As the nonvolatile organic compounds, specifically, there can be cited a lubricant for imparting lubricity to an article, an antirust for imparting an anti-rust effect to metal parts, a moisture-proof coating agent for imparting water repellency to an article, an antifouling coating agent such as a fingerprint removing/preventing agent for imparting antifouling ability to an article, and the like. In the method of forming the coating film of the present invention, it is preferable to use the lubricant as the nonvolatile organic compound from the viewpoint of solubility.

The lubricant means the one which is used for reducing friction on a contact surface and preventing generation of heat and abrasion damage when two members move in a state in which their surfaces are brought into contact with each other. The lubricant may be any form of liquid (oil), semisolid (grease), and solid.

As the lubricant, in terms of excellent solubility to HCFO-1233yd, a fluorine-based lubricant or a silicone-based lubricant is preferable. Note that the fluorine-based lubricant means a lubricant having a fluorine atom in a molecule. Further, the silicone-based lubricant means a lubricant including silicone.

The lubricant included in the coating film-forming composition may be one or a combination of two or more. Each of the fluorine-based lubricant and the silicone-based lubricant may be used alone, or they may be used in combination.

As the fluorine-based lubricant, there can be cited a fluorine-based oil, fluorine-based grease, or a fluorine-based solid lubricant such as resin powder of polytetrafluoroethylene. As the fluorine-based oil, a low polymer of perfluoropolyether or chlorotrifluoroethylene is preferable. As commercial products of the fluorine-based oil, for example, there can be cited product names "Krytox (registered trademark) GPL102" (manufactured by Du Pont Co., Ltd.), "DAIFLOIL #1", "DAIFLOIL #3", "DAIFLOIL #10", "DAIFLOIL #20" "DAIFLOIL #50", "DAIFLOIL #100", "DEMNUM S-65" (these are manufactured by Daikin Industries, Ltd.), and the like.

As the fluorine-based grease, the one in which the fluorine-based oil such as the low polymer of perfluoropolyether or chlorotrifluoroethylene is used as a base oil and powder of polytetrafluoroethylene or other thickeners are compounded is preferable. As commercial products of the fluorine-based grease, for example, there can be cited product names "Krytox (registered trademark) grease 240AC" (manufactured by Du Pont Co., Ltd.), "DAIFLOIL grease DG-203", "DEMNUM L65", "DEMNUM L100", "DEMNUM L200", (these are manufactured by Daikin Industries, Ltd.), "Sumitec F936" (manufactured by SUMICO LUBRICANT CO., LTD.), "Molykote (registered trademark) HP-300", "Molykote (registered trademark) HP-500", "Molykote (registered trademark) HP-870", "Molykote (registered trademark) 6169" (these are manufactured by Dow Corning Toray Co., Ltd.), and the like.

As the silicone-based lubricant, a silicone oil or silicone grease can be cited. As the silicone oils, a dimethyl silicone, a methyl hydrogen silicone, a methyl phenyl silicone, a cyclic dimethyl silicone, an amine group-modified silicone, a diamine group-modified silicone, and a modified silicone oil in which an organic group has been introduced into a side chain or a terminal are preferable. As commercial products of the silicone oil, for example, there can be cited product names "Shin-Etsu Silicone KF-96", "Shin-Etsu Silicone KF-965", "Shin-Etsu Silicone KF-968", "Shin-Etsu Silicone KF-99", "Shin-Etsu Silicone KF-50", "Shin-Etsu Silicone KF-54", "Shin-Etsu Silicone HIVAC F-4", "Shin-Etsu Silicone HIVAC F-5", "Shin-Etsu Silicone KF-56A", "Shin-Etsu Silicone KF-995", "Shin-Etsu Silicone KF-868", "Shin-Etsu Silicone KF-859" (these are manufactured by Shin-Etsu Chemical Co., Ltd.), "SH200" (manufactured by Dow Corning Toray Co., Ltd.), and the like.

As the silicone grease, products in which the various silicone oils cited above are used as a base oil and a thickener such as a metal soap or various additives are compounded are preferable. As commercial products of the silicone grease, for example, there can be cited product names "Shin-Etsu Silicone G-30 Series", "Shin-Etsu Silicone G-40 Series", "Shin-Etsu Silicone FG-720 Series", "Shin-Etsu Silicone G-411", "Shin-Etsu Silicone G-501", "Shin-Etsu Silicone G-6500", "Shin-Etsu Silicone G-330", "Shin-Etsu Silicone G-340", "Shin-Etsu Silicone G-350", "Shin-Etsu Silicone G-630" (these are manufactured by Shin-Etsu Chemical Co., Ltd.), "Molykote (registered trademark) SH33L", "Molykote (registered trademark) 41", "Molykote (registered trademark) 44", "Molykote (registered trademark) 822M", "Molykote (registered trademark) 111", "Molykote (registered trademark) grease for high vacuum", "Molykote (registered trademark) heat diffusion compound" (these are manufactured by Dow Corning Toray Co., Ltd.), and the like.

Further, as the one which can be exemplified as the fluorine-based lubricant and as the silicone-based lubricant, there can be cited a fluorosilicone oil which is a modified silicone oil in which a fluoroalkyl group has been substituted for a terminal or a side chain. As commercial products of the fluorosilicone oil, for example, there can be cited product names "Unidyne (registered name) TG-5601" (manufactured by Daikin Industries, Ltd.), "Molykote (registered trademark) 3451", "Molykote (registered trademark) 3452", (these are manufactured by Dow Corning Toray Co., Ltd.), "Shin-Etsu Silicone FL-5", "Shin-Etsu Silicone X-22-821", "Shin-Etsu Silicone X-22-822", "Shin-Etsu Silicone FL-100" (these are manufactured by Shin-Etsu Chemical Co., Ltd.), and the like.

These lubricants can be used as a coating film for, for example, industrial equipment, tray parts for a CD and a DVD in a personal computer and an audiovisual apparatus, household appliances and office equipment such as a printer, a copier, and a flux device, and the like for which the fluorine-based lubricant is used normally as the coating film. Further, for example, they can be used for a needle and a cylinder of a syringe, medical tube parts, a metal blade, a catheter, and the like for which the silicone-based lubricant is used normally as the coating film.

The antirust means the one which is used for preventing rust of metal materials by covering a surface of metals and blocking oxygen from the metal surface which are easily oxidized by oxygen in the air to generate rust. As the antirusts, there can be cited a mineral oil, and synthetic oils such as polyol esters, polyalkylene glycols, and polyvinyl ethers.

The moisture-proof coating agent and the antifouling coating agent are the ones which are used for imparting a moisture-proof property and an antifouling property to plastic, rubber, metal, glass, a mounted circuit board, and the like. As product examples of the moisture-proof coating agent, there can be cited TOPAS 5013, TOPAS 6013, TOPAS 8007 (manufactured by Polyplastics Co., Ltd.), ZEONOR 1020R, ZEONOR 1060R (manufactured by Zeon Corporation), Apel 6011T, Apel 8008T, (manufactured by Mitsui Chemicals, Inc.), SFE-DP02H, SNF-DP20H (manufactured by AGC SEIMI CHEMICAL CO., LTD.). As product examples of the antifouling coating agent such as a fingerprint preventing agent, there can be cited OPTOOL DSX, OPTOOL DAC (manufactured by Daikin Industries, Ltd.), Fluoro Surf FG-500 (manufactured by Fluoro Technology Co., Ltd.), SR-4000A (manufactured by AGC SEIMI CHEMICAL CO., LTD.), and the like.

The coating film-forming composition is produced normally as a composition in solution form in which the nonvolatile organic compound has been dissolved in the solvent composition of the present invention. A production method of the coating film-forming composition is not particularly limited as long as it is a method of allowing the nonvolatile organic compound to be uniformly dissolved in the solvent composition of the present invention in a predetermined proportion. The coating film-forming composition basically consists of only the nonvolatile organic compound and the solvent composition of the present invention. In the following explanation, the coating film-forming composition using the lubricant as the nonvolatile organic compound is referred to as "lubricant solution". The coating film-forming compositions using other nonvolatile organic compounds are also similar.

A content of the lubricant with respect to a total amount of the lubricant solution is preferably 0.01 to 50 mass %, more preferably 0.05 to 30 mass %, and further preferably 0.1 to 20 mass %. The remainder except the lubricant of the lubricant solution is the solvent composition. As long as the content of the lubricant is in the above-described range, a film thickness of a coating film when the lubricant solution is applied and a thickness of a lubricant coating film after drying are easily regulated in a proper range.

A content of each of the nonvolatile organic compounds such as the antirust, the moisture-proof coating agent, and the antifouling coating agent with respect to a total amount of each of solutions (coating film-forming compositions) in the coating film-forming compositions such as an antirust solution, a moisture-proof coating agent solution, and an antifouling coating agent solution is also preferably in the same range as the above-described content of the lubricant in the lubricant solution.

A coating film consisting of the nonvolatile organic compound can be formed on an article to be coated by applying the coating film-forming composition containing the above-described solvent composition and nonvolatile organic compound on the article to be coated and evaporating the solvent composition from the coating film-forming composition applied on the article to be coated.

As the articles to be coated on which the coating film of the lubricant, the antirust, the moisture-proof coating agent, the antifouling coating agent, or the like is formed, namely, the coating film-forming composition each including these is applied, the articles to be coated made of various materials such as metal, plastic, elastomer, glass, and ceramics can be employed. As specific articles, the articles explained above for each of the nonvolatile organic compounds can be cited.

As an applying method of the coating film-forming composition, for example, there can be cited applying by using a brush, applying by spraying, applying by immersing the articles in the coating film-forming composition, an applying method of bringing the coating film-forming composition into contact with an inner wall of a tube or a needle by pumping up the coating film-forming composition, or the like.

As a method of evaporating the solvent composition from the coating film-forming composition, a publicly known drying method can be cited. As the drying method, for example, air drying, drying by heating, or the like can be cited. A drying temperature is preferably 20 to 100° C.

In the method of forming the coating film of the present invention explained above, either in a state of the solvent composition of the present invention before dissolving these lubricant, antirust, moisture-proof coating agent, and antifouling coating agent, and the like, or in a state of the above-described coating film-forming composition, the use is possible with almost no decomposition in storage or in use.

<Heat Transfer Fluid and Heat Cycle System>

The solvent composition of the present invention can be used as a working fluid (heat transfer fluid) for a heat cycle system. That is, the present invention provides the heat transfer fluid including the solvent composition of the present invention. The heat transfer fluid of the present invention is applicable to the heat cycle system by which materials are heated or cooled.

As the heat cycle systems, there can be cited a Rankine cycle system, a heat pump cycle system, a refrigeration cycle system, a heat transport system, a secondary refrigerant cooling system, and the like. Hereinafter, as one example of the heat cycle system, the refrigeration cycle system will be explained.

The refrigeration cycle system is a system in which the working fluid removes heat energy from a load fluid in an evaporator, thereby cooling the load fluid and cooling it to lower temperature. The refrigeration cycle system is a system constituted of a compressor which compresses a working fluid vapor A to make it into a working fluid vapor B at high temperature and high pressure, a condenser which cools and liquefies the compressed working fluid vapor B to make it into a working fluid C at low temperature and high pressure, an expansion valve which expands the working fluid C emitted from the condenser to make it into a working fluid D at low temperature and low pressure, an evaporator which heats the working fluid D emitted from the expansion valve to make it into the working fluid vapor A at high temperature and low pressure, a pump which supplies a load fluid E to the evaporator, and a pump which supplies a fluid F to the condenser.

The heat transfer fluid of the present invention may include a component other than the solvent composition of the present invention in a range in which the effect of the present invention is not impaired, and preferably consists of only the solvent composition of the present invention. To the heat transfer fluid of the present invention, a lubricating oil can be added. For the lubricating oil, a publicly known lubricating oil to be used for the heat cycle system is used. As the lubricating oils, there can be cited an oxygenated synthetic oil (ester-based lubricating oil, ether-based lubricating oil, and the like), a fluorine-based lubricating oil, a mineral oil, a hydrocarbon-based synthetic oil, and the like.

Moreover, the heat transfer fluid of the present invention is also applicable to a secondary circulation cooling system. The secondary circulation cooling system is a system having a primary cooling device which cools a primary refrigerant consisting of ammonia or a hydrocarbon refrigerant, a secondary circulation cooling device which cools an article to be cooled by circulating a secondary refrigerant for secondary circulation cooling system (hereinafter, referred to as "secondary refrigerant"), and a heat exchanger which exchanges heat between the primary refrigerant and the secondary refrigerant and cools the secondary refrigerant. This secondary circulation cooling system allows cooling of the article to be cooled. The heat transfer fluid of the present invention is suitable for use as the secondary refrigerant.

EXAMPLES

Hereinafter, the present invention will be explained in detail by examples. The present invention is not limited to these examples. Examples 1 to 17 are the examples of the solvent composition of the present invention, and Examples 18 to 21 are comparative examples.

Production Example: Production of HCFC-244ca

In a two-liter four-necked flask in which a glass distillation column (a measured value of five stages in the number of stages) packed with an agitator, a Dimroth, a cooler, and a Rasching ring was placed, 1204 g (9.12 mol) of 2,2,3,3-tetrafluoropropanol (TFPO) and 12 g (0.17 mol) of N,N-dimethylformamide (DMF) were added. 1078 g (9.12 mol) of thionyl chloride was dropped and agitated at a normal temperature for 12 hours. A reactor was heated to 100° C., and reactive distillation was performed at a ratio of 5/1 of reflux time/distillation time by using a reflux timer. Distilled HCFC-244ca was neutralized by a 20 mass % aqueous potassium hydroxide solution. Recovered HCFC-244ca (purity 100%) was 979 g (6.50 mol).

Production Example: Production of HCFO-1233yd and 1-chloro-3,3-difluoro-1-propyne 2000 g of HCFC-244ca was used as a raw material, 19.9 g of tetra-n-butyl ammonium chloride was put in, a reaction temperature was kept at 50° C., and 2792 g of a 40 mass % aqueous potassium hydroxide solution was dropped over 30 minutes. Thereafter, a reaction was continued for 52 hours, and an organic layer was recovered. The recovered organic layer was refined, resulting in obtaining 1520 g of purity 100 mass % HCFO-1233yd(Z) (hereinafter, simply referred to as "HCFO-1233yd(Z)"), 140 g of purity 100 mass % HCFO-1233yd(E) (hereinafter, simply referred to as "HCFO-1233yd(E)"), and 17 g of a mixture containing 5 mass % 1-chloro-3,3-difluoro-1-propyne (the remainder is 95 mass % HCFO-1233yd(E). hereinafter, referred to as "mixture (X)"). This test was repeatedly performed to produce a required amount of each of HCFO-1233yd and 1-chloro-3,3-difluoro-1-propyne.

(Examples 1 to 17: Production of Solvent Composition (Example))

100 g each of solvent compositions containing HCFO-1233yd(Z) and/or HCFO-1233yd(E), and 1-chloro-3,3-difluoro-1-propyne as a stabilizer is prepared so as to each become a proportion of a content presented in Table 1 by using HCFO-1233yd(Z), HCFO-233yd(E), and the mixture (X) obtained in the above. Numeric values of HCFO-1233yd (Z), HCFO-1233yd(E), and 1-chloro-3,3-difluoro-1-propyne presented in Table 1 are each the proportion (mass %) of the content of each of the components to a total of the content of HCFO-1233yd and the content of 1-chloro-3,3-difluoro-1-propyne. Note that the solvent compositions in Examples 1 to 17 are each a solvent composition consisting of only HCFO-1233yd and 1-chloro-3,3-difluoro-1-propyne.

Examples 18 to 21: Production of Solvent Composition (Comparative Example)

Solvent compositions each including HCFO-1233yd(Z) and HCFO-1233yd(E) in the proportion presented in Table 1 and each consisting of only HCFO-1233yd are each produced by using HCFO-1233yd(Z) and HCFO-1233yd(E) obtained in the above.

(Test Example 1: Stability Test)

The obtained solvent compositions in Examples 1 to 21 are retained at 50° C. for three days. Chlorine ion concentrations immediately after the preparation (before the test) and after the retention (after the test) are measured, and stability is evaluated by the following index. Table 1 presents the results. Note that any of concentrations in the index of the evaluation is a chlorine ion concentration.
<Index of Evaluation>
"S (excellent)": less than 10 mass ppm
"A (good)": 10 mass ppm or more and less than 50 mass ppm
"B (slightly poor)": 50 mass ppm or more and less than 100 mass ppm
"x (poor)": 100 mass ppm or more
In the chlorine ion concentration measurement, 40 g of each of the solvent compositions and 40 g of ion-exchange water are put in a 200 mL-capacity separatory funnel, shaken for one minute, and thereafter left still, and an upper-layer aqueous phase obtained by a two-layer separation is separately collected, and the chlorine ion concentration of the aqueous phase is measured by an ion chromatograph (model number: ICS-1000, manufactured by Dionex Corporation).

Test Example 2: Drying Property Test

A drying property is evaluated based on how traces remain when one drop of each of the solvent compositions in Examples 1 to 21 is dropped using a Pasteur pipette and volatilized on a mirror-finished SUS plate under a normal temperature. An index of the evaluation is as follows. Table 1 presents the results.
<Index of Evaluation>
"S (excellent): no trace remains due to complete volatilization of the solvent composition"
"A (good): no trace remains due to almost volatilization of the solvent composition"
"B (possible): a slight residue is recognized, but there is no practical problem"
"x (poor): a visible residue is recognized"

TABLE 1

| Example | HCFO-1233yd(Z) | HCFO-1233yd(E) | 1-chloro-3,3-difluoro-1-propyne | Stability Before test | Stability After test | Drying property |
|---|---|---|---|---|---|---|
| | Proportion (mass %) of content of each of components to total of content of HCFO-1233yd and content of 1-chloro-3,3-difluoro-1-propyne | | | | | |
| 1 | 99.8 | 0.19 | 0.01 | S | A | S |
| 2 | 99.98 | 0.019 | 0.001 | S | S | S |
| 3 | 99.998 | 0.0019 | 0.0001 | S | A | S |
| 4 | 97.9 | 2.0 | 0.1 | S | A | S |
| 5 | 97.99 | 2.00 | 0.01 | S | A | S |
| 6 | 97.999 | 2.000 | 0.001 | S | S | S |
| 7 | 97.9999 | 2.0000 | 0.0001 | S | A | S |
| 8 | 79 | 20 | 1 | S | B | S |
| 9 | 79.9 | 20.0 | 0.1 | S | A | S |
| 10 | 79.99 | 20.00 | 0.01 | S | A | S |
| 11 | 79.999 | 20.000 | 0.001 | S | S | S |
| 12 | 79.9999 | 20.0000 | 0.0001 | S | A | S |
| 13 | 0 | 99 | 1 | S | B | S |

TABLE 1-continued

| Example | HCFO-1233yd(Z) Proportion (mass %) of content of each of components to total of content of HCFO-1233yd and content of 1-chloro-3,3-difluoro-1-propyne | HCFO-1233yd(E) | 1-chloro-3,3-difluoro-1-propyne | Stability Before test | Stability After test | Drying property |
|---|---|---|---|---|---|---|
| 14 | 0 | 99.9 | 0.1 | S | A | S |
| 15 | 0 | 99.99 | 0.01 | S | A | S |
| 16 | 0 | 99.999 | 0.001 | S | S | S |
| 17 | 0 | 99.9999 | 0.0001 | S | A | S |
| 18 | 100 | 0 | — | S | x | S |
| 19 | 0 | 100 | — | S | x | S |
| 20 | 98 | 7 | — | S | x | S |
| 21 | 80 | 20 | — | S | x | S |

As can be seen from Table 1, any of the solvent compositions of the present invention obtained in Examples 1 to 17 indicates that HCFO-1233yd can be stably retained. In Examples 18 to 21 as the comparative examples, it is found that HCFO-1233yd is decomposed to some extent. Further, the solvent compositions of the present invention obtained in Examples 1 to 17 indicate that no trace remains in the drying test and it volatilizes similarly to the solvent compositions in Examples 18 to 21 consisting of only HCFO-1233yd.

Test Example 3: Stability Evaluation Test by Accelerated Oxidation Test

Regarding the solvent compositions in Examples 1 to 17 (examples) and Examples 18 to 21 (comparative examples) obtained in the above, an accelerated oxidation test for confirming stability in a reflux time of 48 hours is conducted in conformity to an accelerated oxidation test of JIS K 1508-1982. That is, in 200 mL of each of the solvent compositions, under a condition in which a test piece of carbon steel for machine structural use (S20C) is made to coexist in a gas phase and a liquid phase, while passing oxygen bubbles saturated with moisture, light is irradiated by an electric bulb, and reflux is performed for 48 hours by heat generation of the electric bulb.

Chlorine ion concentrations before and after the above-described accelerated oxidation test are measured, and the stability is evaluated by the following index. Further, degrees of a change in test piece appearance before and after the above-described accelerated oxidation test are evaluated by the following index. Table 2 presents the results.

<Index of Stability Evaluation>
Any of the following concentrations in the index of the evaluation is a chlorine ion concentration.
"S (excellent)": less than 10 mass ppm
"A (good)": 10 mass ppm or more and less than 50 mass ppm
"B (slightly poor)": 50 mass ppm or more and less than 100 mass ppm
"x (poor)": 100 mass ppm or more
<Index of Test Piece Appearance Evaluation>
"S (excellent)": there is no change before and after the test.
"A (good)": a gloss has been slightly lost after the test compared with before the test, but there is no practical problem.
"B (slightly poor)": a surface after the test slightly rusts.
"x (poor)": rust is recognized on the entire surface of the surface after the test.

Test Example 4: Evaluation of Cleaning Ability

Regarding the solvent compositions in Examples 1 to 17 (examples) and Examples 18 to 21 (comparative examples) obtained in the above, each of the following cleaning tests A to D is performed, and Table 2 presents the results.

[Cleaning Test A]
After immersing a test piece (25 mm×30 mm×2 mm) of SUS-304 in a product name "Daphne Magplus HT-10" (manufactured by Idemitsu Kosan Co., Ltd.) which is a cutting oil, the test piece is immersed in 50 mL of the solvent composition in each of the examples for one minute and pulled up, and degrees to which the cutting oil has been removed are observed. Evaluation of detergency is performed in accordance with the following criteria.
"S (excellent)": the cutting oil is completely removed.
"A (good)": the cutting oil is almost removed.
"B (slightly poor)": the cutting oil remains in trace amounts.
"x (poor)": the cutting oil considerably remains.

[Cleaning Test B]
A test is conducted similarly to the cleaning test A except to use a product name "Daphne Magplus AM20" (manufactured by Idemitsu Kosan Co., Ltd.) as a cutting oil, and detergency is evaluated by the same criteria.

[Cleaning Test C]
A test is conducted similarly to the cleaning test A except to use a product name "Daphne Magplus HM25" (manufactured by Idemitsu Kosan Co., Ltd.) as a cutting oil, and detergency is evaluated by the same criteria.

[Cleaning Test D]
A test is conducted similarly to the cleaning test A except to use a product name "G-6318FK" (manufactured by NIHON KOHSAKUYU CO., LTD.) as a cutting oil, and detergency is evaluated by the same criteria.

Test Example 5: Evaluation of Ability as Dilution Coating Solvent

The solvent compositions in Examples 1 to 17 (examples) and Examples 18 to 21 (comparative examples) obtained in the above are used as dilution coating solvents, and coating film-forming compositions (lubricant solutions) are prepared to evaluate ability.

The solvent composition in each of the examples and a product name "Krytox (registered trademark) GPL102" (manufactured by Du Pont Co., Ltd., fluorine-based oil) which is a fluorine-based lubricant are mixed with each other so that a content of the fluorine-based lubricant is 0.5 mass % with respect to a total amount of the coating film-forming composition, and the coating film-forming compositions are prepared.

Next, on a surface of an aluminum deposited sheet in which aluminum has been deposited on a sheet made of iron, the obtained coating film-forming compositions are each applied in a thickness of 0.4 mm and air-dried under a condition of 19° C. to 21° C., thereby each forming a lubricant coating film on the aluminum deposited sheet surface. The evaluation of the ability as the dilution coating solvents of the solvent compositions when the lubricant coating films are formed is performed as follows. Table 2 presents the results.

[Dissolved State]

A dissolved state of the coating film-forming composition using the solvent composition in each of the examples is visually confirmed to be evaluated by the following criteria.

"S (excellent)": immediately uniformly dissolved to become transparent.

"A (good)": if shaken, uniformly dissolved to become transparent.

"B (slightly poor)": slightly cloudy.

"x (poor)": cloudy or phase-separated.

[Coating Film State]

A state of the lubricant coating film formed by the coating film-forming composition using the solvent composition in each of the examples is visually confirmed to be evaluated by the following criteria.

"S (excellent)": a uniform coating film is formed.

"A (good)": an almost uniform coating film is formed.

"B (slightly poor)": nonuniformity is partially seen on the coating film.

"x (poor)": nonuniformity is considerably seen on the coating film.

examples even in a case of performing the accelerated oxidation test. Further, as presented in Table 2, it is found that the solvent compositions in the examples of the present invention are capable of sufficiently cleaning and removing the cutting oil and have excellent detergency similarly to the solvent compositions in Examples 18 to 21 to which no stabilizer is added in any cleaning test.

Moreover, as present in Table 2, it is obvious that the lubricant solvents using the solvent compositions of the present invention as the dilution coating solvents are excellent in solubility of the lubricant and capable of simply forming uniform lubricant coating films similarly to the solvent compositions in Examples 18 to 21 which have no stabilizer in any applying test.

Test Example 5: Evaluation of Detergency and Feeling for Clothing

A white cardigan of wool fabric is cleaned using the solvent composition of the present invention to evaluate a state of detergency and feeling as follows.

10 L (15 kg) of the solvent composition in Example 6 is prepared at the beginning. Moreover, 75 g (0.5 mass % with respect to a total amount of the solvent composition) of NF-98 (manufactured by NICCA CHEMICAL CO., LTD.: brand name "NF-98") is added to the solvent composition as soap and stirred well, to make a test solvent to be used for the cleaning test.

The above-described cardigan which has been worn and become dirty is cut in half, and one of the ones cut in half is used for the cleaning test. For the test cleaning, a dry cleaning tester (brand name: DC-1A, manufactured by DAIEI KAGAKU SEIKI MFG. CO., LTD.) is used, the above-described test solvent and the article to be cleaned are

TABLE 2

| Example | Stability by accelerated oxidation test | | | | Detergency | | | | Ability as dilution coating solvent | |
|---|---|---|---|---|---|---|---|---|---|---|
| | Chlorine ion concentration | | Test piece appearance after test | | | | | | Coating | |
| | Before test | After test | Gas phase | Liquid phase | Test A | Test B | Test C | Test D | Dissolved state | film state |
| 1 | S | A | S | A | S | S | S | S | S | S |
| 2 | S | S | S | S | S | S | S | S | S | S |
| 3 | S | A | S | A | S | S | S | S | S | S |
| 4 | S | A | S | A | S | S | S | S | S | S |
| 5 | S | A | S | A | S | S | S | S | S | S |
| 6 | S | S | S | S | S | S | S | S | S | S |
| 7 | S | A | S | A | S | S | S | S | S | S |
| 8 | S | B | B | B | S | S | S | S | S | S |
| 9 | S | A | S | A | S | S | S | S | S | S |
| 10 | S | A | S | A | S | S | S | S | S | S |
| 11 | S | S | S | S | S | S | S | S | S | S |
| 12 | S | A | S | A | S | S | S | S | S | S |
| 13 | S | B | B | B | S | S | S | S | S | S |
| 14 | S | A | S | A | S | S | S | S | S | S |
| 15 | S | A | S | A | S | S | S | S | S | S |
| 16 | S | S | S | S | S | S | S | S | S | S |
| 17 | S | A | S | A | S | S | S | S | S | S |
| 18 | S | x | x | x | S | S | S | S | S | S |
| 19 | S | x | x | x | S | S | S | S | S | S |
| 20 | S | x | x | x | S | S | S | S | S | S |
| 21 | S | x | x | x | S | S | S | S | S | S |

It can be said that it is obvious from Table 2 that any of the solvent compositions in the examples is more excellent in stability than the solvent compositions in the comparative put in a cleaning tank whose capacity is about 11 L, and cleaning is performed at a normal temperature for ten minutes. Thereafter, the cleaned cardigan is taken out of the cleaning tank and sufficiently dried, and the cleaning ability and the feeling are evaluated compared with the remaining half cardigan which has not been cleaned. For comparison, a similar cleaning test is performed on 1,1,3,3-pentafluorobutane (HFC-365mfc) and 1,1,2,2-tetrafluoroethyl-2,2,2-trifluoroethyl ether (HFE-347pc-f) which are conventional cleaning solvents.

The cardigan cleaned by the test solvent based on the solvent composition in Example 6 has the detergency and the feeling equal to those when it is cleaned by the conventional cleaning solvents.

A solvent composition of the present invention is a stable solvent composition which is excellent in solubility of various organic substances and excellent in detergency and has a sufficient drying property, and has no adverse effect on a global environment and is stabilized to suppress decomposition. This solvent composition is useful for a wide range of industrial uses such as cleaning and applying uses and can be used for articles of various materials such as metal, plastic, and elastomer without giving adverse effects.

What is claimed is:

1. A coating film-forming composition comprising:
   a solvent composition comprising 1-chloro-2,3,3-trifluoro-1-propene and 1-chloro-3,3-difluoro-1-propyne, and
   a nonvolatile organic compound.

2. The coating film-forming composition according to claim 1, wherein a proportion of a content of 1-chloro-3,3-difluoro-1-propyne to a total of a content of the 1-chloro-2,3,3-trifluoro-1-propene and a content of the 1-chloro-3,3-difluoro-1-propyne is 0.0001 to 0.1 mass %.

3. The coating film-forming composition according to claim 1, wherein a proportion of a content of 1-chloro2,3,3-trifluoro-1-propene to a total amount of the solvent composition is 80 mass % or more.

4. The coating film-forming composition according to claim 1, wherein the 1-chloro-2,3,3-trifluoro-1-propene consists of (Z)-1-chloro-2,3,3- trifluoro-1-propene and (E)-1-chloro-2,3,3-trifluoro-1-propene, and a proportion of a content of (Z)-1-chloro-2,3,3-trifluoro-1-propene to a total amount of 1-chloro-2,3,3-trifluoro-1-propene is 80 to 100 mass %.

5. A method of forming a coating film, comprising dissolving a nonvolatile organic compound in the coating film-forming composition according to claim to prepare a coating film-forming composition and evaporating the solvent composition after applying the coating film-forming composition on an article to be coated, to form a coating, film consisting of the nonvolatile organic compound.

6. The coating film-forming composition according to claim 1, wherein the nonvolatile organic compound is at least one selected from a group consisting of a lubricant, an antirust, a moisture-proof coating agent, and an antifouling coating agent.

* * * * *